United States Patent [19]

Daidone

[11] Patent Number: 4,529,777

[45] Date of Patent: Jul. 16, 1985

[54] DENTAL CASTING RESIN FROM ACRYLIC MONOMER, ACRYLIC RESIN, AND VINYL CHLORIDE RESIN

[76] Inventor: Philip Daidone, 12 Ivy Hill Dr., Matawan, N.J. 07747

[21] Appl. No.: 440,443

[22] Filed: Nov. 10, 1982

[51] Int. Cl.³ .................. C08L 27/06; C08L 33/08; C08L 33/10; C08L 35/02
[52] U.S. Cl. .................. 525/193; 525/227; 525/309; 525/304; 525/305; 433/171; 106/35
[58] Field of Search .................. 525/193, 309

[56] References Cited

U.S. PATENT DOCUMENTS

| | | | |
|---|---|---|---|
| 2,315,503 | 4/1943 | Crowell | 525/193 |
| 3,957,916 | 5/1976 | Tanno et al. | 525/193 |
| 4,115,479 | 9/1978 | Daidone | 525/193 |

Primary Examiner—Carman J. Seccuro
Attorney, Agent, or Firm—Evelyn M. Sommer

[57] ABSTRACT

A dental casting resin wherein the finished casting has a combined vinyl resin content of from 5 to 60% by wt. prepared by polymerizing liquid monomer, e.g. methyl methacrylate, in the presence of at least one vinyl resin and at least one acrylic resin, wherein said monomer is a non-solvent at room temperature for said vinyl resin and wherein the volume ratio of solid resins to liquid monomer is at least about 3.5:1.

13 Claims, No Drawings

DENTAL CASTING RESIN FROM ACRYLIC MONOMER, ACRYLIC RESIN, AND VINYL CHLORIDE RESIN

This invention relates to dental casting resins and more particularly to casting resins having a vinyl resin content of from 5 to 60% by wt. in which the volume ratio of solid resins to liquid monomer is at least about 3.5:1 which are suitable for use as dental resins and to a process for the preparation of such casting resins.

Dispersions of finely-divided vinyl chloride resins suspended in liquid plasticizers have been introduced under the term plastisols. These dispersions are fluid at ordinary temperatures, but on heating and subsequent cooling, they are converted to solid, elastomeric compositions due to solvation of the dispersed resin particles by the plasticizer. Heretofore, only very flexible elastomers have been made from plastisols because the amount of plasticizer required to yield a fluid dispersion or paste with the finely-divided vinyl chloride resin is so high that when the resin is ultimately elasticized with the plasticizer, the resulting elastomer is quite flexible and soft.

In U.S. Pat. No. 2,618,621, there is described a method for preparing modified plastisols which are fluid at ordinary temperatures but which will set up after a heating and cooling cycle to moderately rigid to semi-rigid elastomers. This is accomplished by replacing part of the usual plasticizer employed in plastisols with a methacrylate diester of a liquid polyethelene glycol. In the liquid state, this ester serves as part of the dispersant for the suspended particles of the vinyl chloride resin, but on heating it polymerizes. On cooling the gelled mass, the polymeric ester forms part of the colloidal composition but it is less effective as a plasticizer then the usual nonpolymeric ester plasticizers. Consequently, the elastomer is stiffer.

Thus, it is known that plastic compositions may be formed by mixing a high molecular weight polymer with a vulcanizable plasticizer which is capable of polymerizing on heating and then heating the mixture to form a mass of reduced thermoplasticity.

In my U.S. Pat. No. 4,115,479, I describe a dental casting resin wherein the furnished casting has a combined vinyl resin content of from 20 to 65% prepared by polymerizing the liquid monomer, for instance methyl methacrylate, in the presence of (a) vinyl resin, e.g. polyvinylchloride or polyvinylchloride-polyvinylidene chloride copolymer, having a particle size within the range of 0.2 to 5 microns and (b) vinyl resin, which can be the same or different as the (a) resin, having a particle size within the range of 15-150 microns, wherein the monomer is a non-solvent at room temperature for the vinyl resin. In this casting resin, the particle sizes of the vinyl resin are particularly important and the liquid monomer constitutes from 30-80% by weight of the entire composition.

Most dentures are made by compression molding and curing in hot water after closure of a mold under pressure and transfer to another press to hold compression. It is desired that the finished denture product conform to the model from which it is made as completely as is possible and this is termed "fit". The finished denture is also designed to maintain vertical, i.e. to fit the other half of the model called the counter. The cured resin (denture) is removed from the model for various finish processing. When the denture is thereafter placed back on the model, dimensional changes have usually occurred leaving a space between the denture and the model in the palate area. The usual ratio of components of powder (resin) to monomer (liquid phase) usually varies, between 3 volumes of powder to 1 volume of monomer down to 1:1 wherein one relies on pressure on the polymerizing melt to force additional resin into the void as shrinkage occurs due to volume changes upon polymerization. While the casting provide a very good fit, a new dental casting resin has now been discovered which provides an even better fit.

It is accordingly the object of this invention to provide a new dental casting resin which provides an improved fit to the mold model and which maintains its adaptation and fit to the model on standing. These and other objects of the invention will become apparent to those skilled in this art from the following description of the invention.

The present invention broadly comprises a dental casting resin in which the finished casting has a combined vinyl resin content of from 5 to 60% by wt. prepared by polymerizing liquid monomer in the presence of at least one vinyl resin and at least one acrylic resin in which the monomer is a non-solvent at room temperature for the vinyl resin and wherein the volume ratio of solid resins to liquid monomer is at least about 3.5:1.

The present invention is similar to the dental casting resin of my aforesaid prior U.S. Pat. No. 4,115,479, the disclosure of which is hereby incorporated by reference, in that:

1. The polymerizable plasticizer must be compatible with the vinyl resins and their conventional ester plasticizers both as a monomer and a polymer;
2. The monomer must not solvate the vinyl resin at ordinary temperature otherwise the plastisols tend to gel and become too viscous; and
3. The polymerizable monomer must be capable of curing rapidly in the presence of the usual peroxide catalysts at elevated temperatures to provide a hard resin with the flexural strength adapting the resin to use as an engineering plastic and more particularly to use as a dental resin.

The present invention differs from my prior casting resin in that it is no longer necessary to strictly observe the particle size ranges for the vinyl resins of 0.2-5 and 15-150 microns and in that the volume ratio of solid resins to liquid monomer is at least about 3.5:1.

The amount of vinyl resins, preferably vinyl chloride resins, employed in the formulation of the casting compositions of this invention amount to from 5 to 60% by wt. In order that the casting resin will be moldable for application purposes, it is necessary that the amount of vinyl resins do not exceed about 60% by wt. of the entire compositions. If desired, although not necessary, the two types of vinyl resins employed in my prior patent can be used, namely a vinyl resin having a particle size within the range of 0.2-5 microns and a vinyl resin having a particle size in the range of 15-150 microns, preferably 15-30 microns in a ratio of 1-5:5-1.

There is a limit to the amount of vinyl resin which can be present in the composition due to the fact that, in general, most vinyl resins have a very high absorption rate for the methacrylate monomer and therefore maintenance of a suitably low viscosity for a time sufficient to effect satisfactory casting is not possible. Too high a viscosity gives rise to flow problems i.e. flow under compression and therewith undesirable porosity, incomplete mold filling and the like.

The monomer, for instance methacrylate mono and-/or diester, or combinations thereof, is employed in an amount such that the ratio of solid resins to monomer is at least about 3.5:1 by volume. On a weight basis, the ratio is at least 2.6:1, i.e. the liquid monomer is up to about 28% by wt. of the composition. Preferably the monomer is 20–28% by wt. As the resultant stiffness and hardness increase with increasing concentration of the dimethacrylate, the amount thereof, ie. its concentration in the solvent component has to be selected so that the cured resin product will have the desired hardness and flexural modulus of elasticity.

In order to facilitate curing of the monomer, it is preferable to incorporate from 0.01 to 1.0% by weight of the monomer of a peroxide polymerization catalyst such as benzoyl peroxide, acetyl peroxide, t. butyl perbenzoate, lauroyl peroxide, and the like. In order to inhibit premature polymerization of the monomer in the plastisol, a polymerization inhibitor, such as hydroquinone or the methyl ether of hydroquinone may be added.

The vinyl chloride resins employed in the making of the dispersions may be copolymers of vinyl chloride with other polymerizable materials such as vinyl acetate, vinyl propionate, methyl acrylate, butyl acrylate, methyl methacrylate, butyl methacrylate, acrylonitrile, vinylidine chloride and maleate esters such as dibutyl maleate or the vinyl chloride resins may be delta or gamma polyvinyl chloride. To secure compositions of good physical properties, it is desirable that the vinyl chloride resins be of high molecular weights, as determined by their relative insolubility in certain solvents, such as toluene and butyl acetate. In making the copolymers, vinyl chloride is usually employed in predominant amount. The preferred resins are copolymers of vinyl chloride and vinyl acetate containing 95 to 99% vinyl chloride, and polyvinyl chloride.

To obtain dispersions of adequate fluidity, it is essential to start with finely-divided resins. Mechanical methods of sub-division are, in general, not wholly satisfactory because of the limitation on the particle size of the resins obtainable. It is preferable to employ a vinyl chloride resin which is made by polymerization of the monomeric materials in aqueous emulsion, according to known procedures, for instance, by polymerization at low temperatures of 35° to 40° C.

The monomer component can be methyl methacrylate, ethyl methacrylate, butyl methacrylate, isobutyl methacrylate, isopropyl methacrylate, the corresponding acrylates, hydroxyacrylates and hydroxymethacrylates and their mixtures; diethylene glycol dimethacrylate, triethylene glycol dimethacrylate and tetraethylene glycol dimethacrylate and their mixtures.

In forming the dispersion, the vinyl chloride resins are intimately mixed with the monomer so that the vinyl resin constitutes 5–60% by wt. of the composition. There are added to the vinyl resins prior to addition of the monomer solvent, any pigments, stabilizers, powdered filling materials and flame-proofing ingredients desired. Conventional plasticizers for the vinyl chloride resins which may be present include di(2-ethylhexyl)phthalate, dicapryl phthalate, tri(2-ethylhexyl)phosphate, butyl phthalyl butyl glycollate, dibutyl and dioctyl sebecate, di(2-ethylhexyl)succinate, tricresyl phosphate, the diesteramide of diethanolamine with 2-ethylhexanoic acid and the like.

The resin portion of the formulation includes one or more acrylic resins. The amount of acrylic resin present will depend to a considerable extent on the amount of vinyl resin present in the specific formulation. The acrylic resin should preferably have a particle size in the coarse range and namely should exceed the size of 15 microns. Such a resin can be a methyl methacrylate resin or cross-linked methyl methacrylate resin for instance with a dimethacrylate.

When the casting is intended for teeth or a denture base, the resin particles are preferably capable of being translucent. The use of suspension grade or emulsion resin polyvinyl chloride or copolymers of polyvinyl chloride have been found to perform this function well.

The resin formulations may be made by the same methods now practiced, i.e. by stirring the vinyl chloride resins in the monomer by grinding the resins and the monomer on a three-roll mill.

The preferred general procedure involves admixing the fine and coarse vinyl resin components and then dispersing the mixture in the monomer under rapid agitation. It is, however, possible to introduce the coarse vinyl resin component into the monomer having dispersed therein the fine resin component.

The resin formulation is placed in the mold wherein the polymerization takes place under elevated temperature. The mold is transferred into a press where the polymerization can be carried out under slightly elevated pressures of up to 100 psig, or even higher.

In order to more fully illustrate the invention, the following examples are presented by way of illustration, parts and percentages being by weight unless otherwise specifically noted.

In carrying out the examples, a resin-monomer mixture was prepared by dispersing thirty cubic centimeters (30 cc) of an acrylic powder (methyl methacrylate dental grade polymer—Type 12, produced by Sartomer Company) in 10 c.c. of monomer containing equal parts of methyl methacrylate monomer and dimethacrylate monomer. The components were admixed and then conventionally pressure cast in boiling water three times.

EXAMPLE 1

State of the Art powder to liquid volume ratio of 3:1.

Example 1 was repeated but in this instance, 30 cc of the acrylic powder was dispersed in 10 cc of a mixture of vinyl resin (Geon 202 of B. F. Goodrich) dispersed in the acrylic monomer (2 g.+8 g). These components were admixed and then conventionally pressure cast in boiling water three times. This mixture is equivalent to a powder to liquid volume ratio of 4:1. The resulting palatal space of the three 3:1 volume ratio castings were 0.006, 0.007 and 0.006 inch respectively. The palatal space with the three 4:1 castings were 0.002, 0.003 and 0.002 inch respectively. These results demonstrate a substantial decrease in the magnitude of the palatal space, i.e. a better fit, with the resins of the invention.

The above procedure was followed using the procedure as described above in polymer-monomer relationships as hereinafter described with the results set out in the table. It is clear that it is only when a powder to liquid volume ratio greater than 3:1, i.e. at least 3.5:1 is employed that the desired result with respect to the fit of the denture are achieved.

Various changes and modifications can be made in the products and process of this invention without departing from the spirit and scope thereof. The various embodiments which have been described herein are for the purpose of further illustrating the invention but were not intended to limit it.

TABLE

| Ex. No. | Polymer-Monomer | % monomer | Fit | Fit | Fit** |
|---|---|---|---|---|---|
| 1. (art) | 30 cc acrylic powder<br>10 cc acrylic monomer | 33.3 | .006 | .006 | .007 |
| 2. | 30 cc acrylic/vinyl powder (8 + 2)*<br>10 cc vinyl/acrylic monomer (2 + 18) | 26.7 | .002 | .003 | .002 |
| 3. (art) | 30 cc vinyl/acrylic powder (2 + 8)<br>10 cc acrylic monomer | 33.3 | .006 | .005 | .005 |
| 4. | 30 cc vinyl/acrylic powder (2 + 18)<br>10 cc vinyl/acrylic monomer (2 + 8) | 26.7 | .002 | .002 | .001 |
| 5. | 30 cc acrylic powder<br>12 cc vinyl/acrylic monomer (2 + 10) | 31.25 | .003 | .004 | .002 |
| 6. | 30 cc acrylic powder<br>10 cc vinyl/acrylic monomer (1 + 9) | 30.0 | .002 | .003 | .002 |
| 7. | 40 cc acrylic/vinyl powder (80:20)<br>10 cc acrylic monomer | 27.4 | .002 | .002 | .001 |
| 8. | 35 cc acrylic/vinyl powder (80:20)<br>10 cc acrylic monomer | 30.2 | .002 | .001 | .002 |

*grams
**inches

What is claimed is:

1. A dental casting resin wherein the finished casting has a combined vinyl resin content of from 5 to 60% by weight prepared by polymerizing a liquid monomer selected from the group consisting of monomethacrylates and dimethacrylates, in the presence of at least one vinyl resin selected from the group consisting of vinyl chloride polymer and copolymers of vinyl chloride with at least one of vinyl acetate, vinyl propionate, methyl acrylate, butyl acrylate, methyl methacrylate, butyl methacrylate, acrylonitrile, vinylidine chloride and dibutyl maleate and at least one acrylic resin selected from the group consisting of methyl methacrylate and cross-linked methyl methacrylate wherein said monomer is a non-solvent at room temperature for said vinyl resin and wherein the volume ratio of solids resins to liquid monomer is at least about 3.5:1.

2. The dental casting resin of claim 1 wherein the vinyl resin comprises a vinyl resin having a particle size within the range of 0.2 up to about 150 microns.

3. The dental casting resin of claim 2 wherein the vinyl resin component having a particle size within the range of 0.2-150 microns has a majority of particles falling within the range of 15-30 microns.

4. The dental casting resin of claim 1 wherein the monomer is at least one member selected from the group consisting of methyl methacrylate, ethyl methacrylate, butyl methacrylate, isobutyl methacrylate, isopropyl methacrylate, methyl acrylate, ethyl acrylate, butyl acrylate, isobutyl acrylate, isopropyl acrylate, methyl hydroxy methacrylate, ethyl hydroxy methacrylate, butyl hydroxy methacrylate, isobutyl hydroxy methacrylate, isopropyl hydroxy methacrylate, methyl hydroxy acrylate, ethyl hydroxy acrylate, butyl hydroxy acrylate, isobutyl hydroxy acrylate, isopropyl hydroxy acrylate, ethylene glycol dimethacrylate, triethylene glycol dimethacrylate tetraethylene glycol dimethacrylate, ethylene glycol diacrylate, triethylene glycol diacrylate, and tetraethylene glycol diacrylate.

5. The dental casting resin according to claim 1 wherein said polymerization is carried out in the presence of a peroxide catalyst.

6. The dental casting resin according to claim 1 wherein said polymerization is carried out in the presence of a tertiary aromatic amine as promoter.

7. The dental casting resin of claim 1 wherein the vinyl resin is a vinyl chloride homopolymer or copolymer.

8. The dental casting resin according to claim 7 wherein the vinyl resin is a vinyl chloride homopolymer.

9. The dental casting resin according to claim 1 wherein said volume ratio is about 4:1.

10. A method of making the dental casting resin according to claim 1 which comprises polymerizing liquid monomer in the presence of at least one vinyl resin and at least one acrylic resin, wherein the volume ratio of solid resin to liquid monomer is at least about 3.5:1 and said monomer is a non-solvent at room temperature for said vinyl resin, for a sufficiently long period of time to allow said resin to be cast.

11. The method of claim 10 wherein said vinyl resin comprises a vinyl resin having a particle size within the range of 0.2-150 microns.

12. The method of claim 10 wherein said polymerization is carried out at an elevated temperature.

13. A denture characterized by superior fit, high textural strength and high impact strength produced by the process of claim 10.

* * * * *